(12) United States Patent
Brocas et al.

(10) Patent No.: US 11,814,336 B2
(45) Date of Patent: Nov. 14, 2023

(54) OLIGOMERIC ALKOXY AMINES

(71) Applicant: Arkema France, Colombes (FR)

(72) Inventors: Anne-Laure Brocas, Peyrehorade (FR); Sylvain Bourrigaud, Morlanne (FR); Sylvie Cazaumayou, Dax (FR); Ilias Iliopoulos, Paris (FR)

(73) Assignee: Arkema France, Colombes (FR)

( * ) Notice: Subject to any disclaimer, the term of this patent is extended or adjusted under 35 U.S.C. 154(b) by 283 days.

(21) Appl. No.: 17/046,603

(22) PCT Filed: Apr. 17, 2019

(86) PCT No.: PCT/FR2019/050918
§ 371 (c)(1),
(2) Date: Oct. 9, 2020

(87) PCT Pub. No.: WO2019/202262
PCT Pub. Date: Oct. 24, 2019

(65) Prior Publication Data
US 2021/0139415 A1   May 13, 2021

(30) Foreign Application Priority Data
Apr. 19, 2018  (FR) ...................................... 1853448

(51) Int. Cl.
| | | |
|---|---|---|
| *C07C 239/20* | (2006.01) | |
| *C08F 2/38* | (2006.01) | |
| *C08K 5/32* | (2006.01) | |
| *C08F 220/18* | (2006.01) | |
| *C07F 9/40* | (2006.01) | |
| *C08F 2/06* | (2006.01) | |
| *C08F 220/14* | (2006.01) | |

(52) U.S. Cl.
CPC .......... *C07C 239/20* (2013.01); *C07F 9/4006* (2013.01); *C08F 2/06* (2013.01); *C08F 2/38* (2013.01); *C08F 220/14* (2013.01); *C08F 220/1804* (2020.02); *C08K 5/32* (2013.01)

(58) Field of Classification Search
CPC ............. C07F 239/20; C08F 2/38; C08K 5/32
See application file for complete search history.

(56) References Cited

FOREIGN PATENT DOCUMENTS

| | | |
|---|---|---|
| FR | 1325521 A | 4/1963 |
| JP | 6089452 A | 5/1985 |
| WO | 2016097646 A1 | 6/2016 |

OTHER PUBLICATIONS

Cuatepotzo-Díaz et al., "Nitroxide mediated polymerization using diphenyl azabutane N-oxides. A study of electronic effects and of the [nitroxide]/[initiator] ratio on the polymerization control," Polymer, 45 (2004) 815-824. (Year: 2004).*
International Search Report and Written Opinion for International Application No. PCT/FR2019/050918, dated Jan. 15, 2020, 14 pages.

(Continued)

Primary Examiner — Catherine S Branch
(74) Attorney, Agent, or Firm — RatnerPrestia

(57) ABSTRACT

A new class of alkoxyamines, exhibiting improved stability on storage, especially in the presence of monomers and/or of solvent is described, particularly where the alkoxylamines are a new class of oligomeric alkoxyamines, which are obtained by addition of one or more monomeric entities to an alkoxyamine.

2 Claims, 1 Drawing Sheet

(56) References Cited

OTHER PUBLICATIONS

Nakamura et al., "Free Radical Initiation Mechanisms in the Polymerization of Methyl Methacrylate and Styrene with 1,1,3,3-Tetramethylbutyl Peroxypivalate: Addition of Neopentyl Radicals", Journal of the American Chemical Society, vol. 119, No. 45, Nov. 1997, pp. 10987-10991.
Garrett et al., "Reactivity of Polyolefins toward Cumyloxy Radical: Yields and Regioselectivity of Hydrogen Atom Transfer", Macromolecules, vol. 47, No. 2, Jan. 10, 2014, pp. 544-551.
Giglio et al., "Metal-Free, Aerobic Dioxygenation of Alkenes Using Simple Hydroxamic Acid Derivatives", Journal of the American Chemical Society, vol. 133, No. 34, Aug. 31, 2011, pp. 13320-13322.
Connolly et al., "Reactions of the "Stable" Nitroxide Radical TEMPO. Relevance to "Living" Free Radical Polymerizations and Autopolymerization of Styrene", Tetrahedron Letters, vol. 38, vol. 7, Feb. 17, 1997, pp. 1133-1136.
Xia et al., "Catalyst-Controlled Dioxygenation of Olefins: An Approach to Peroxides, Alcohols and Ketones", Journal of Organic Chemistry, vol. 80, No. 11, May 19, 2015, pp. 5572-5580.

\* cited by examiner

OLIGOMERIC ALKOXY AMINES

CROSS-REFERENCE TO RELATED APPLICATIONS

This is the national phase of International Application No. PCT/FR2019/050918, filed Apr. 17, 2019, which claims priority to French Application No. 1853448, filed Apr. 19, 2018. The disclosure of each of these applications is incorporated herein by reference in its entirety for all purposes.

FIELD OF THE INVENTION

The present invention concerns a new class of alkoxyamines, exhibiting improved stability on storage, especially in the presence of monomers and/or of solvent.

The present invention concerns more particularly a new class of oligomeric alkoxyamines, which are obtained by addition of one or more monomeric entities to an alkoxyamine.

The present invention also concerns the use of these oligomeric alkoxyamines for synthesizing polymers and copolymers, and also the polymers obtained with this new class of oligomeric alkoxyamines.

The present invention also concerns the compositions comprising this new class of oligomeric alkoxyamines in the presence of monomer and/or of solvent.

Technical Problem

Alkoxyamines are molecules which allow the controlled radical polymerization of monomers exhibiting double bonds (vinylic, styrenic, (meth)acrylic, etc.). This provides access to the synthesis of block copolymers.

This technology, though widely described in the literature, retains a low profile in the industrial sphere, since there are obstacles remaining: lack of compatibility with certain monomers, incomplete conversion, inadequate stability under certain conditions, more particularly in the presence of the monomers used for producing (co)polymers, or else of solvent.

In the industrial implementation of the synthesis of copolymers by controlled radical polymerization in the presence of alkoxyamines, it is necessary, however, to leave the alkoxyamines for several hours, or even several days, in the presence of monomers in intermediate storage or premixing reactors, and at unregulated temperatures.

Therefore, in view of the lack of reproducibility in the syntheses conducted by the applicant, numerous studies were carried out, and have shown the lack of stability of an alkoxyamine-monomer system, sometimes even at well below the temperature conditions used for the polymerization.

These studies have shown that the issue is not a commencement of polymerization, but a degradation of the alkoxyamine, but have not been able to provide a mechanism or an explanation.

The applicant has therefore conducted new studies with the aim of eliminating or mitigating this problem.

The applicant has found that the alkoxyamines, when added to a certain reduced number of monomeric units, exhibited the desired character of stability. Stability refers to the low reactivity of a given alkoxyamine in the presence of monomer, at a certain temperature, but also to the consistency of the reactivity of an alkoxyamine left in a solvent for a given time.

These new entities, which are oligomeric alkoxyamines, retain their character of initiating and controlling radical polymerization reactions. In the presence of monomer, they are more stable over time at a given temperature, limiting the polymerization reactions. In the presence of solvent, they retain their kinetic character of radical initiation over time.

SUMMARY OF THE INVENTION

The invention relates to the alkoxyamines of the formula:

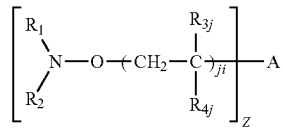

i: monomer number of the monomer j
j: type of monomer
i taking the values from 1 to 12
j taking the values from 1 to 12
and $1 =< iXj =< 12$
A is a cyclic or noncyclic hydrocarbon group with or without a heteroatom, and may contain at least one metallic species. This is the initiator fragment of the initial alkoxyamine used for preparing the alkoxyamine of the invention;
$R_1$ is a cyclic or noncyclic hydrocarbon group with or without a heteroatom, and may contain at least one metallic species.
$R_2$ is a cyclic or noncyclic hydrocarbon group with or without a heteroatom, and may contain at least one metallic species.
$R_1$ and $R_2$ may or may not form part of the same cyclic structure.
$R_3$ is hydrogen or a hydrocarbon group with or without a heteroatom, and may contain at least one metallic species.
$R_4$ is a cyclic or noncyclic hydrocarbon group with or without a heteroatom, and may contain at least one metallic species.
Z is an integer of between 1 and 10, limits included.

DETAILED DESCRIPTION

Figure 1:
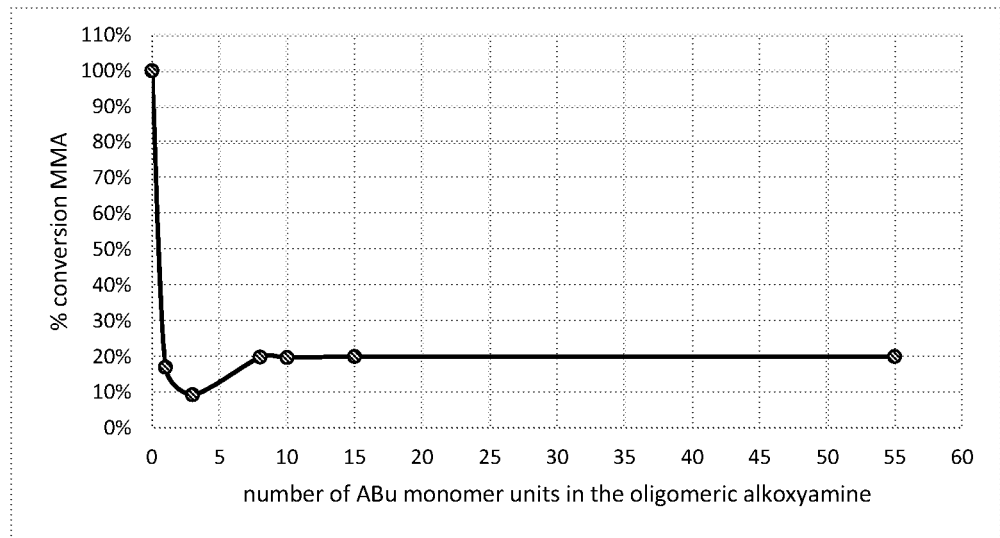
FIG. 1 shows a graph of MMA conversion as a function of the number of monomer entities in the alkoxyamine.

The oligomeric alkoxyamines which are a subject of the invention are obtained by addition of the alkoxyamines (1) to at least one monomer (2) exhibiting a double bond.

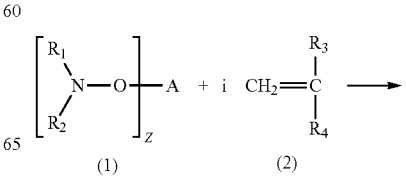

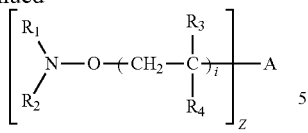

When the alkoxyamines (1) are added to a plurality of monomeric units, the units may be of the same monomer or of different monomers—hence the more general formula of the alkoxyamines that are a subject of the invention:

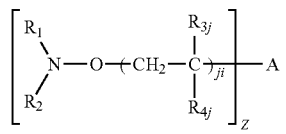

In this case, j is the type of monomer and i is the monomer number of the monomer j.
- i: monomer number of the monomer j
- j: type of monomer
- i taking the values from 1 to 12
- j taking the values from 1 to 12
- and $1 = \!< i \times j = \!< 12$ and preferably $2 = \!< i \times j = \!< 12$ and more preferably $2 = \!< i \times j = \!< 8$.

j represents the type of monomer. Preference will be given to using a single type of monomer in the context of the invention, although two different types of monomer and even three different types of monomer may be used. There is no limit on the different types of monomers which can be used; however, to remain within the scope of the invention, their number will be fixed at 12.

When a single type of monomer is used, any type of monomer which carries a double bond may be used, though preference will be given to selecting functional or nonfunctional acrylates, and preferably alkyl acrylates, and more preferably butyl acrylate, but also styrenic monomers, and preferably styrene.

With regard to z, it represents the functionality of the alkoxyamine in terms of initiating and nitroxide entities. Accordingly, for a value of z=2, the alkoxyamine will be a di-alkoxyamine; for a value of z=3, it will be a tri-alkoxyamine, etc. Z is an integer of between 1 and 10, limits included, preferably of between 1 and 4, limits included, and more preferably of between 2 and 3, limits included.

Any type of alkoxyamine may be used in the context of the invention. Thus the applicant has demonstrated that with two very different alkoxyamines, the addition thereof to a certain reduced number of monomeric units presented the desired character of stability.

The preferred alkoxyamines are preferably those for which the nitroxide (also called controller fragment) is selected from the following:
the nitroxides of formula:

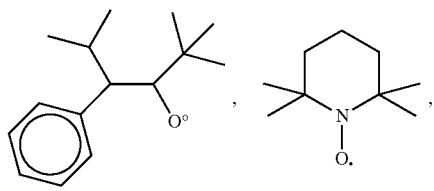

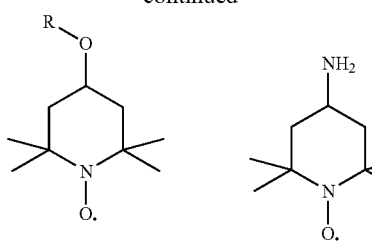

(where R = H, alkyl fragment, SO2-Ph, SO2Me, Na, K),

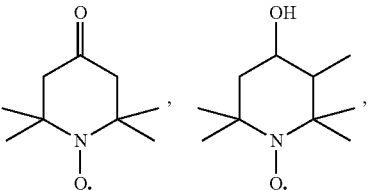

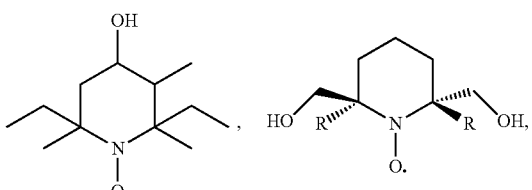

(where R = Me or Et)

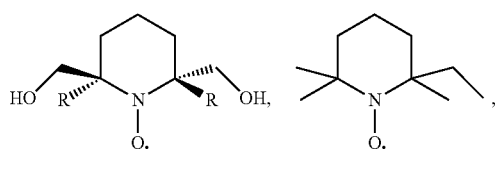

(where R = Me or Et)

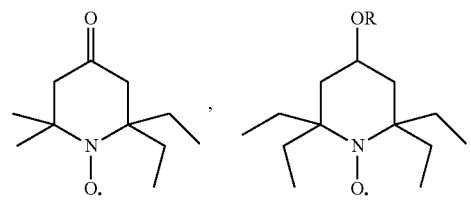

(where R = H or Me)

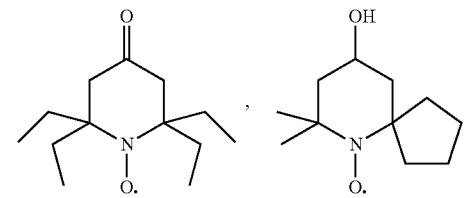

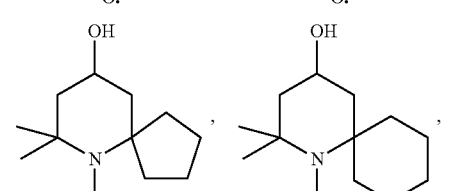

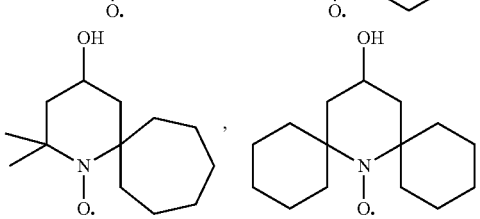

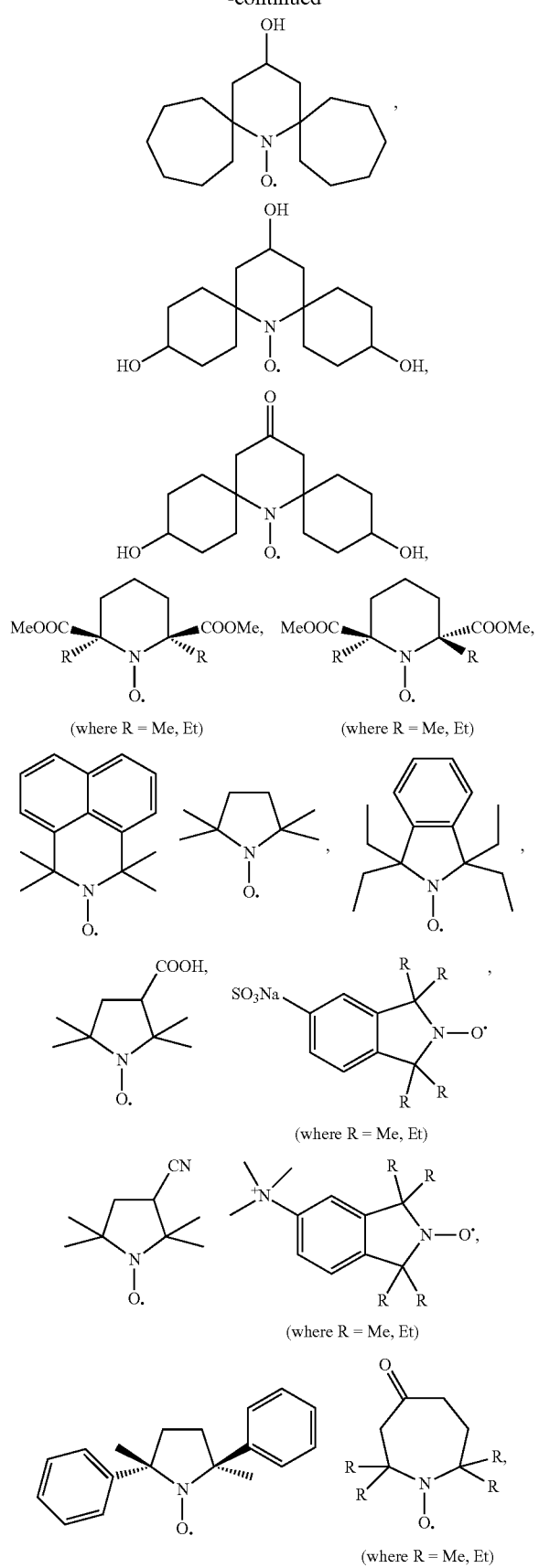
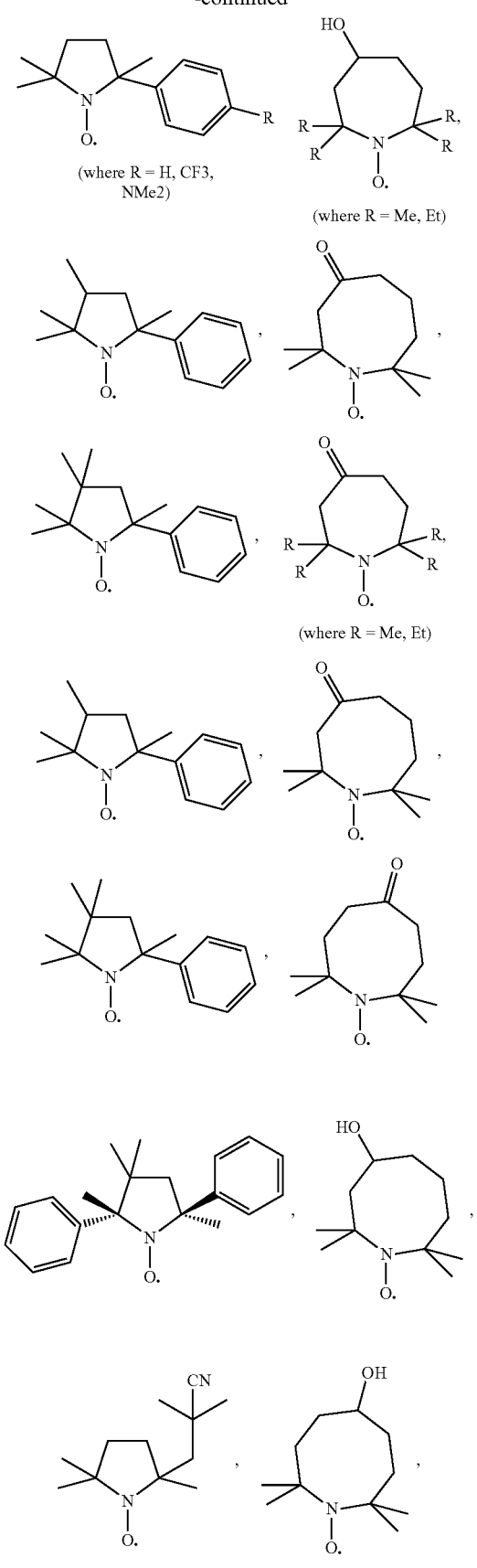

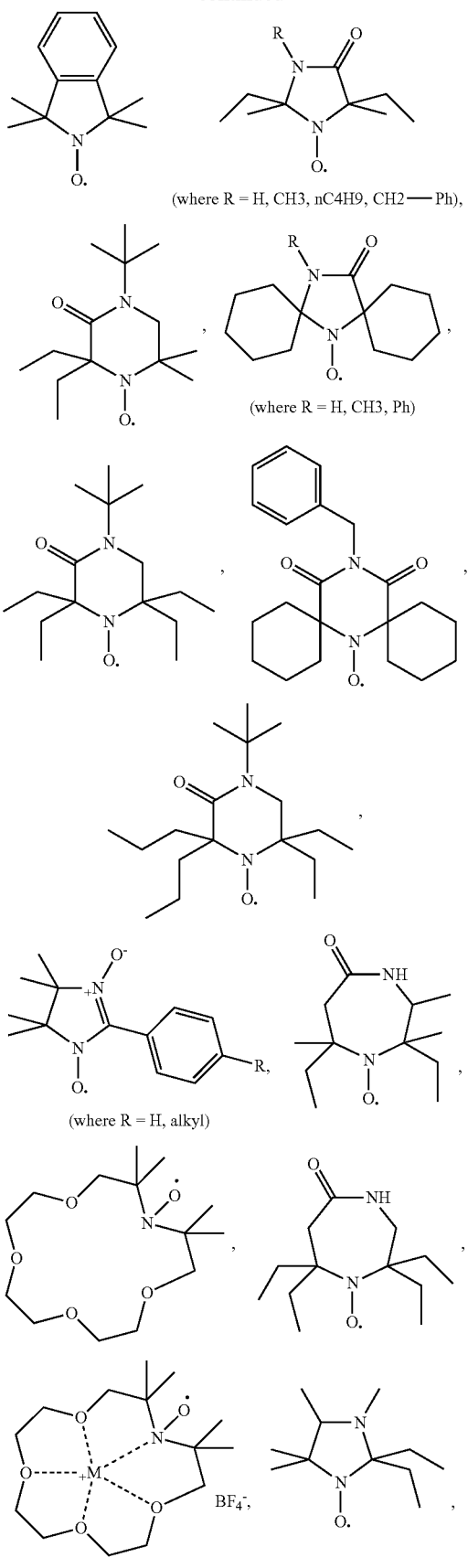
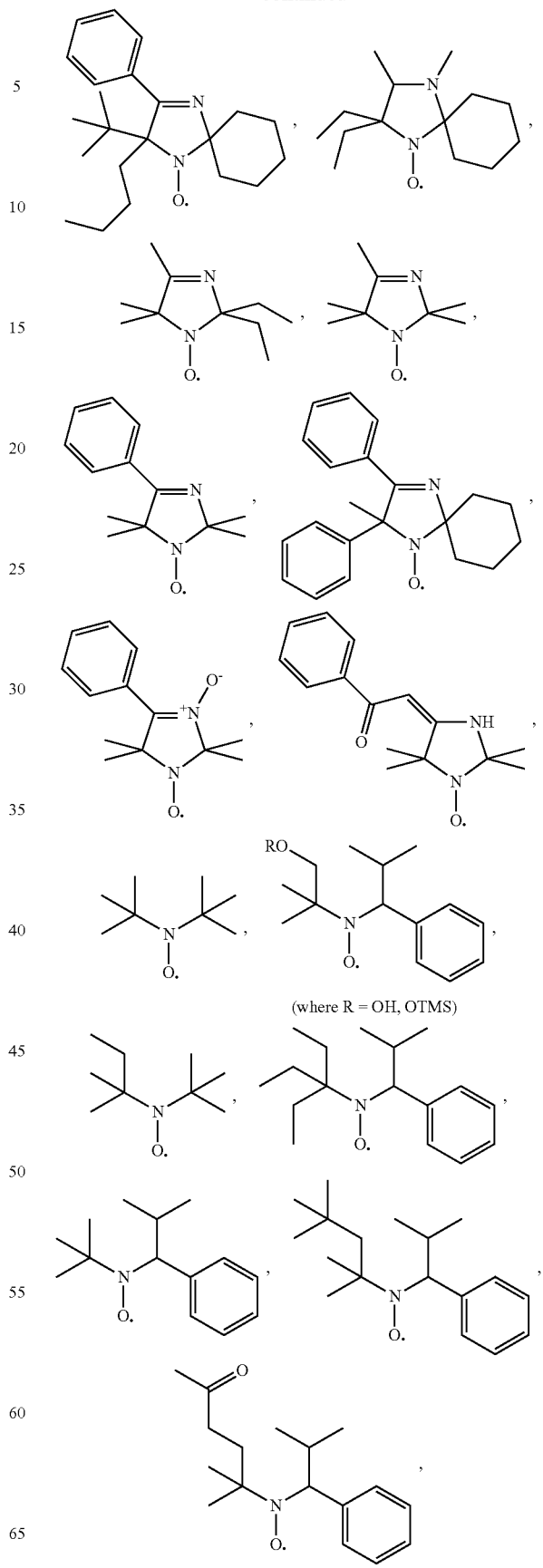

-continued
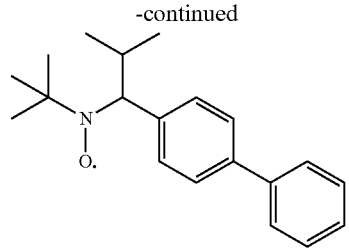
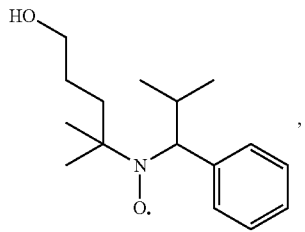
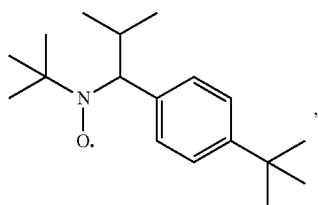
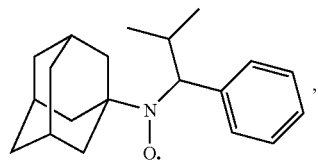
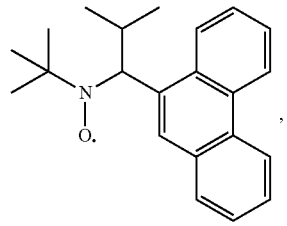
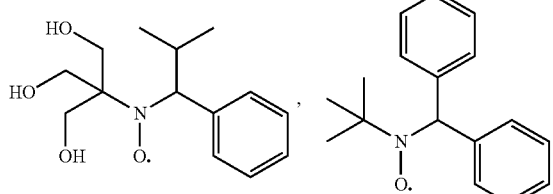
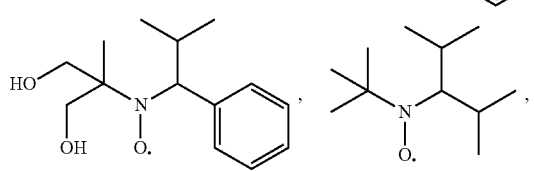
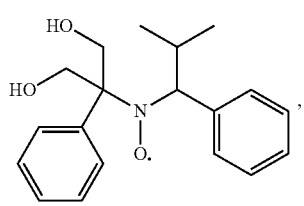
-continued
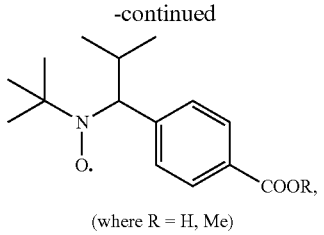
(where R = H, Me)
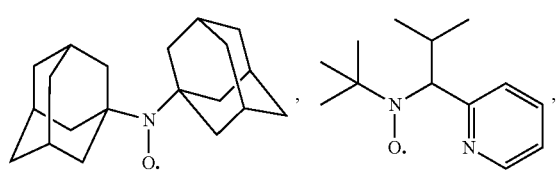
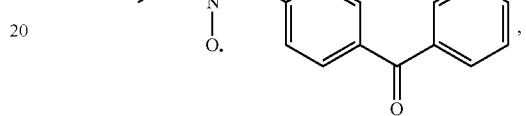
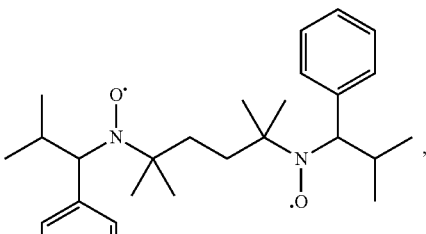
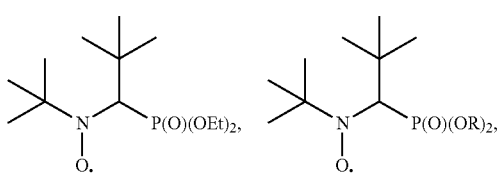
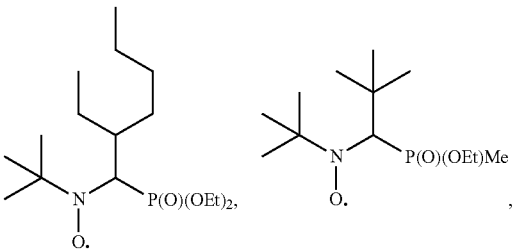
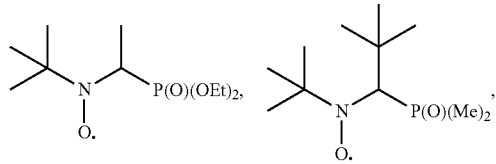
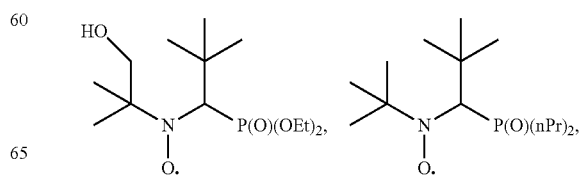

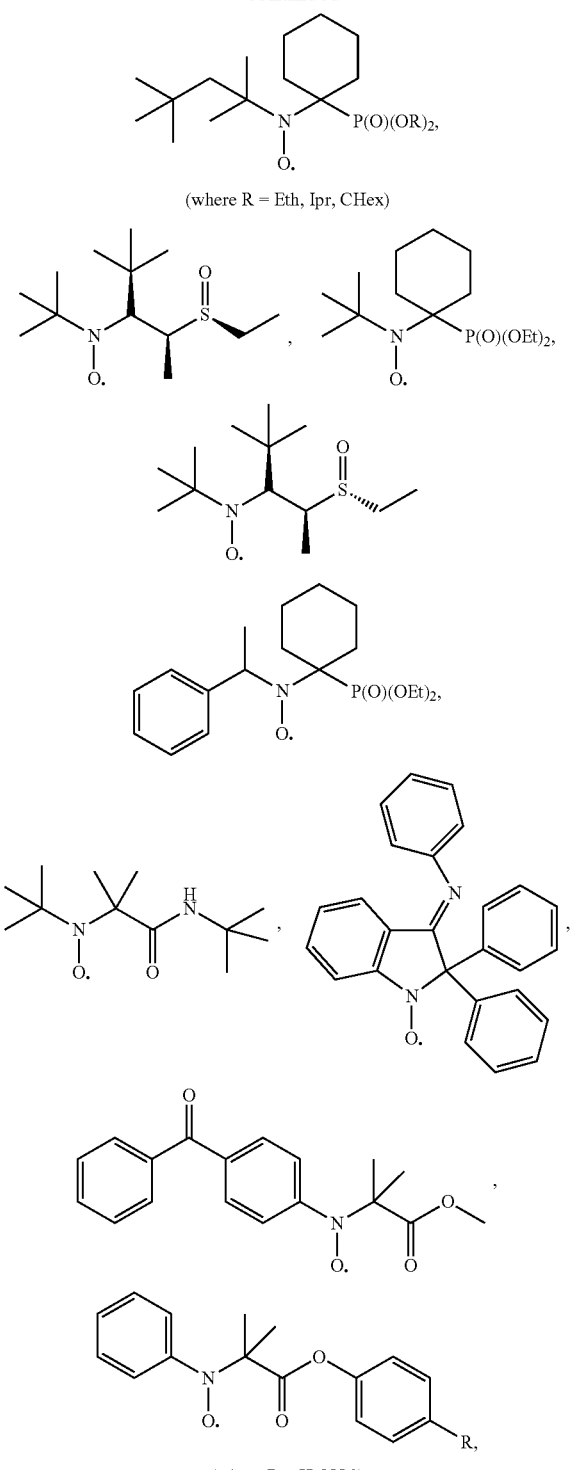
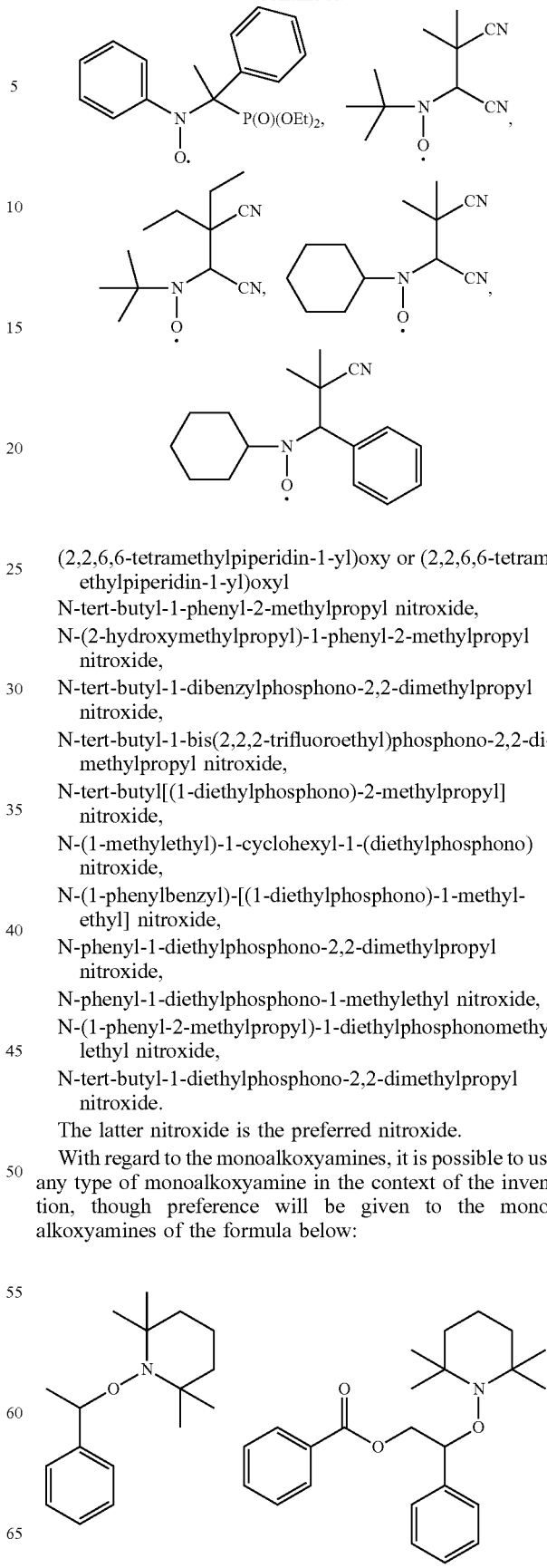

(2,2,6,6-tetramethylpiperidin-1-yl)oxy or (2,2,6,6-tetramethylpiperidin-1-yl)oxyl
N-tert-butyl-1-phenyl-2-methylpropyl nitroxide,
N-(2-hydroxymethylpropyl)-1-phenyl-2-methylpropyl nitroxide,
N-tert-butyl-1-dibenzylphosphono-2,2-dimethylpropyl nitroxide,
N-tert-butyl-1-bis(2,2,2-trifluoroethyl)phosphono-2,2-dimethylpropyl nitroxide,
N-tert-butyl[(1-diethylphosphono)-2-methylpropyl] nitroxide,
N-(1-methylethyl)-1-cyclohexyl-1-(diethylphosphono) nitroxide,
N-(1-phenylbenzyl)-[(1-diethylphosphono)-1-methylethyl] nitroxide,
N-phenyl-1-diethylphosphono-2,2-dimethylpropyl nitroxide,
N-phenyl-1-diethylphosphono-1-methylethyl nitroxide,
N-(1-phenyl-2-methylpropyl)-1-diethylphosphonomethylethyl nitroxide,
N-tert-butyl-1-diethylphosphono-2,2-dimethylpropyl nitroxide.

The latter nitroxide is the preferred nitroxide.

With regard to the monoalkoxyamines, it is possible to use any type of monoalkoxyamine in the context of the invention, though preference will be given to the monoalkoxyamines of the formula below:

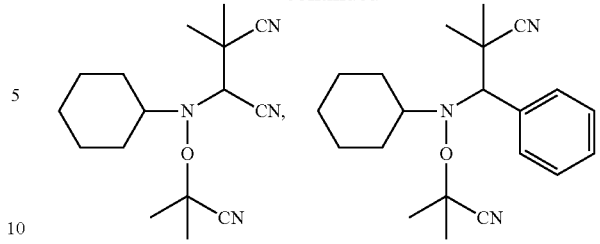
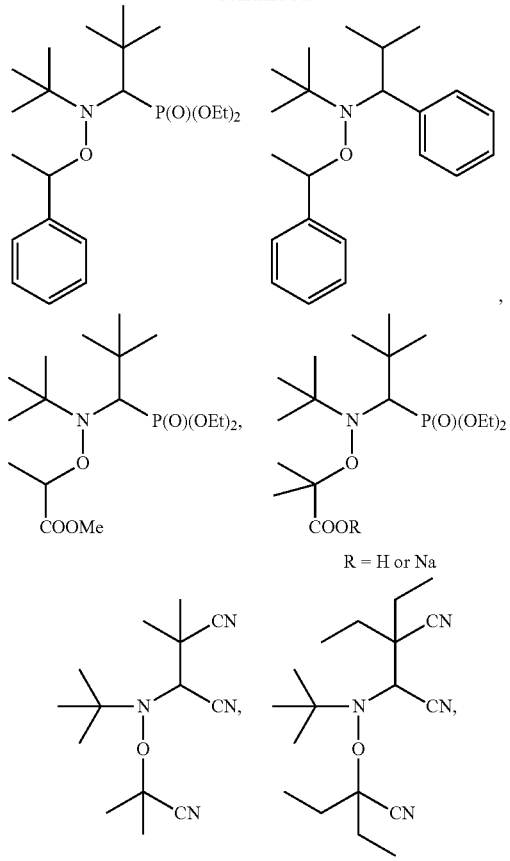
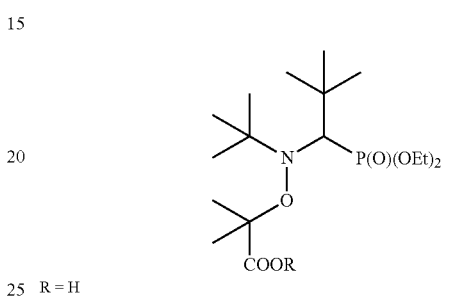
More particularly, the following monoalkoxyamine will be selected:
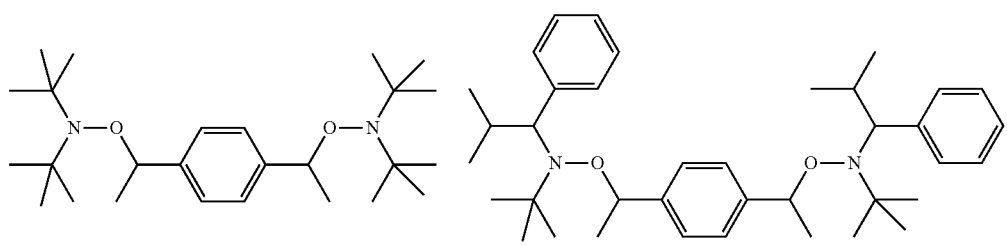
R = H
With regard to the dialkoxyamines, it is possible to use any type of dialkoxyamine in the context of the invention; however, preference will be given to the dialkoxyamines of the formula below:
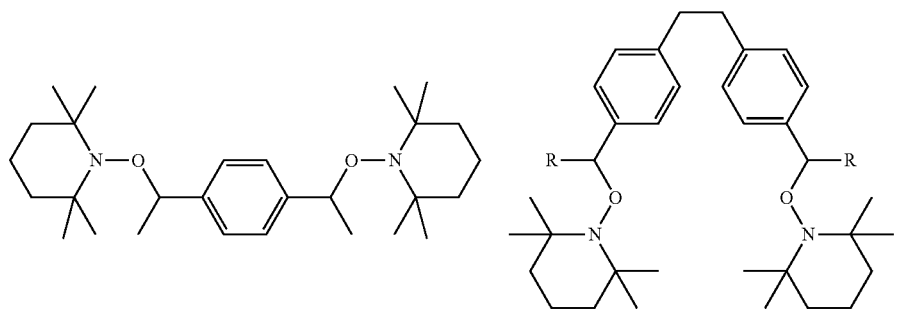

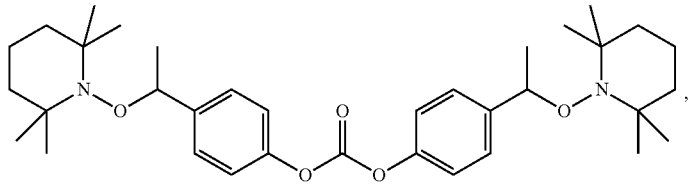
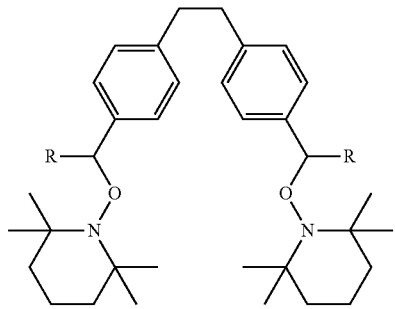
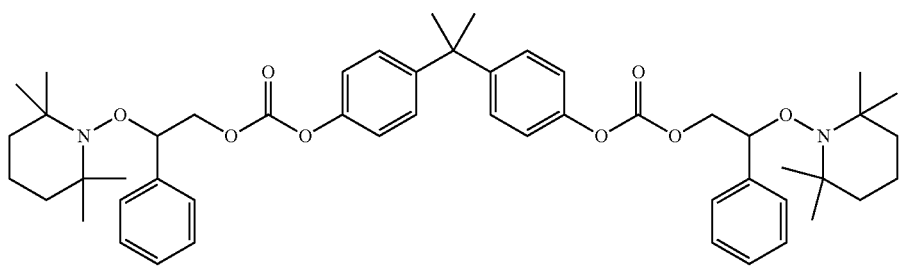
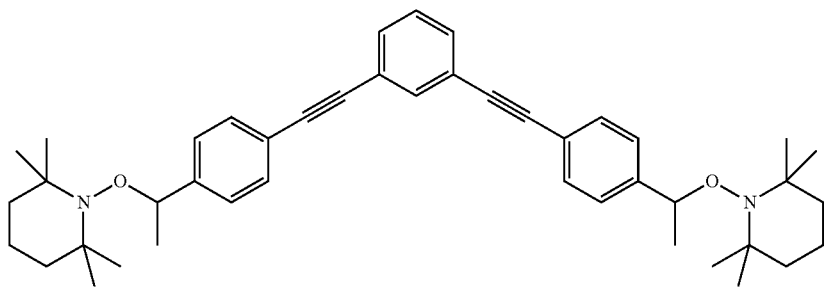
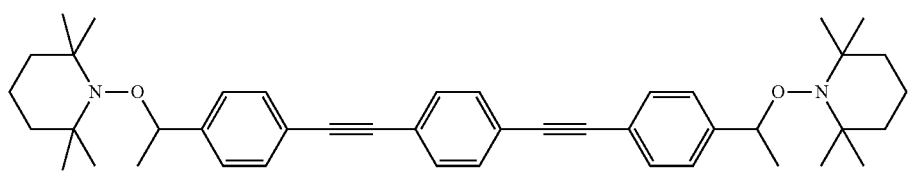
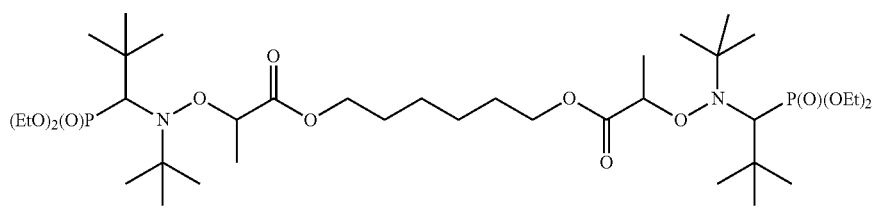
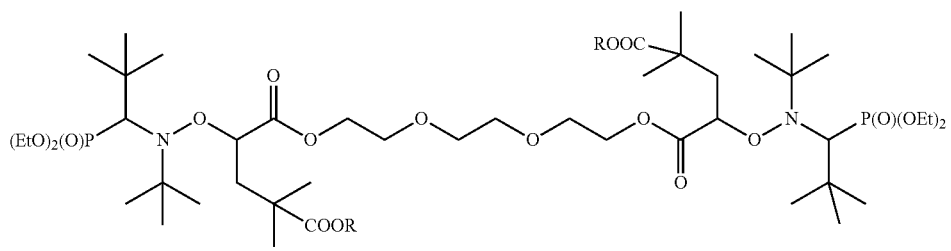

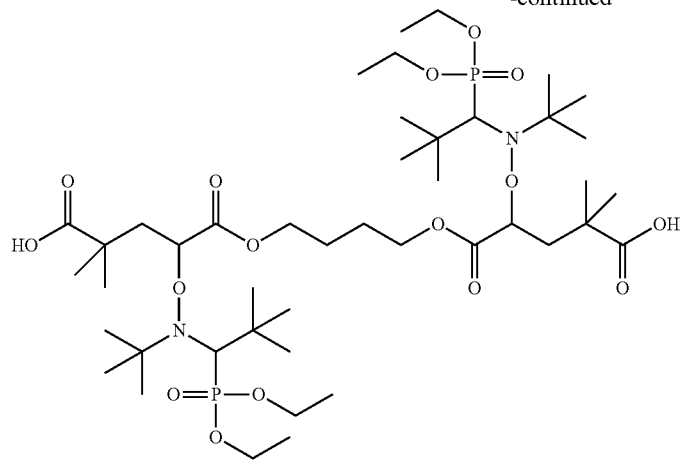
where R = H or Na
Preference will be given more particularly to the following structures:
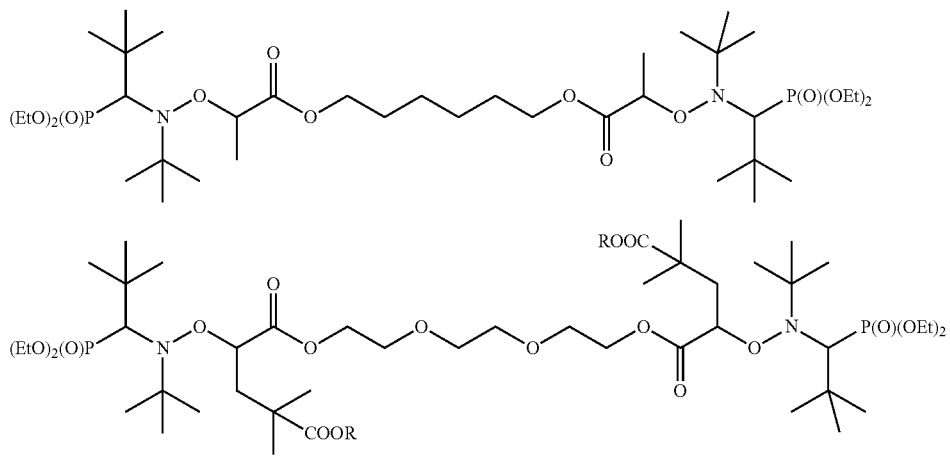
where R = H
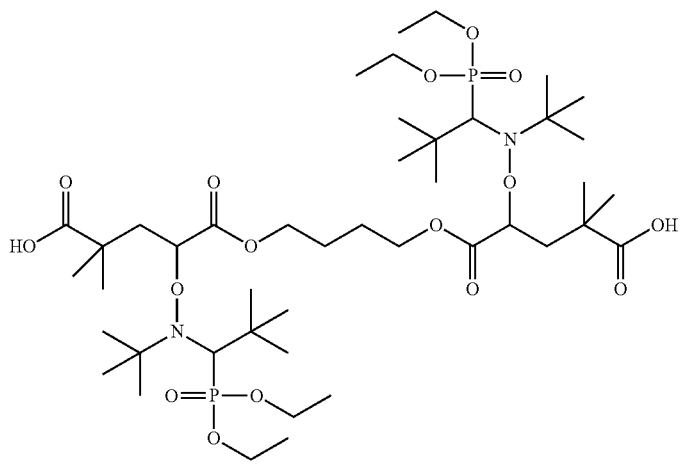

More preferably still, the following dialkoxyamine will be selected:

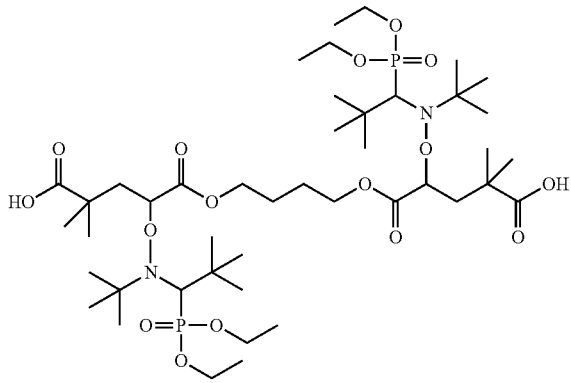 [SMILES: CCOP(=O)(OCC)C(N(OC(CC(C)(C)C(=O)O)C(=O)OCCCCOC(=O)C(CC(C)(C)C(=O)O)ON(C(C(C)(C)C)P(=O)(OCC)OCC)C(C)(C)C)C(C)(C)C)C(C)(C)C]

Regarding the trialkoxyamines, it is possible to use any type of trialkoxyamine in the context of the invention, although preference will be given to the trialkoxyamine of the formula below:

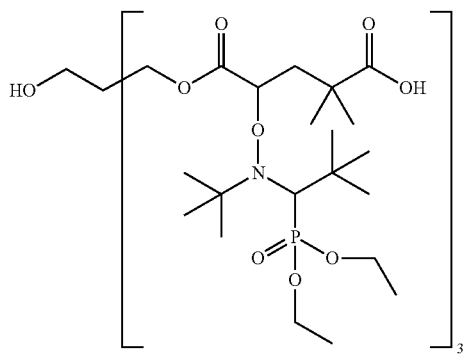

The present invention also relates to the use of these oligomeric alkoxyamines for synthesizing polymers and copolymers, and also to the polymers obtained with the alkoxyamines that are a subject of the invention, encompassing homopolymers, random copolymers, block (diblock, triblock, multiblock) copolymers.

The present invention also relates to the use of these oligomeric alkoxyamines for grafting these oligomeric alkoxyamines on a surface.

The present invention also relates to the compositions comprising this new class of oligomeric alkoxyamines and monomer(s) and/or solvent(s). The solvent in question may be any type of solvent, polar or apolar, but preferably apolar. With regard to the monomers, the species in question may be any type of monomer or entity possessing at least one double bond ((co)polymeric oligomer), but preferably comprises acrylates or methacrylates such as alkyl (meth)acrylates, preferably butyl acrylate, styrenic monomers such as styrene or mixtures thereof, with a proportion by mass of oligomeric alkoxyamine that can range from 0.1 to 60% and preferably from 1 to 50%, and more preferably from 1 to 30%, limits included.

Example 1

The starting alkoxyamine used is N-(2-methylpropyl)-N-(1-diethylphosphono-2,2-dimethylpropyl)-O-(2-carboxyprop-2-yl)hydroxylamine, which has the following structural formula:

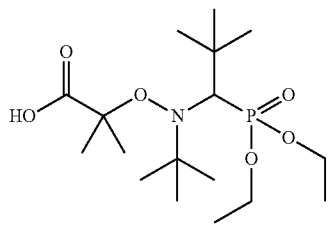 [SMILES: CCOP(=O)(OCC)C(N(OC(C)(C)C(=O)O)C(C)(C)C)C(C)(C)C]

It is available from Arkema under the name Blocbuilder®

Synthesis of the Oligomer where n=1
(Blocbuilder®+1 Unit of Butyl Acrylate)

31 g of BlocBuilder® are introduced into 844 g of toluene and 15 g of butyl acrylate (ABu). The solution is homogenized for 30 minutes and then introduced into a stainless steel reactor by pressure reduction. The solution is heated to 110° C. for 1 hour and then at 115° C. until a butyl acrylate conversion of 70% is obtained (verified by means of a thermal balance). The solution is recovered and then dried under vacuum for 24 hours at ambient temperature.

The oligomers n=3, 8, 10, 15 and 55 are produced in exactly the same way. For n=1 to 15, the solutions are prepared with a concentration by mass of 3.5% of Blocbuilder®, relative to the total mass of the mixture. For n=55, the concentration by mass of Blocbuilder® is 1.6% (table 1).

TABLE 1

| Number of monomer units incorporated into the alkoxyamine | Mass of Blocbuilder ® (g) | Mass of ABu (g) | Mass of toluene (g) |
|---|---|---|---|
| 1 | 31 | 15 | 844 |
| 3 | 33 | 47 | 862 |
| 8 | 33 | 127 | 783 |
| 10 | 31 | 149 | 688 |
| 15 | 33 | 237 | 673 |
| 55 | 16 | 443 | 541 |

Example 2: Stability of the Oligomer in a Methyl Methacrylate (MMA) Solution at 47° C.

0.6 g of oligomer synthesized in example 1 (n=1) is introduced into a 30 mL flask. The methyl methacrylate is introduced until a total mass of 20 g is obtained. The solution is stirred for 30 minutes. 8 g are withdrawn and introduced into a hermetic bottle with a magnetic bar, and the bottle is then crimped. The environment is then placed under nitrogen in order to remove the dioxygen present. The bottle is placed in a water bath at 47° C. for 24 hours. After 24 hours, the solids content of the mixture is determined by means of a thermal balance (set from 20 to 125° C. in 30 s).

Each sample is prepared with a constant percentage of active center (number of chains); an active center is considered to be one Blocbuilder® entity. For n=0, 3, 8, 10, 15 and 55, the same procedure is repeated. (table 2)

TABLE 2

| The number of monomer units incorporated into the alkoxyamine | Mass of the oligomer or of Blocbuilder® (n = 0) in g | Mass of MMA (g) |
| --- | --- | --- |
| 0 | 0.46 | 19.54 |
| 1 | 0.6 | 19.4 |
| 3 | 0.9 | 19.1 |
| 8 | 1.8 | 18.2 |
| 10 | 1.94 | 18.06 |
| 15 | 3 | 17 |
| 55 | 8.8 | 11.2 |

The dry extract measurements show a development of the degree of conversion as a function of the number of monomer units incorporated into the alkoxyamine (table 4); the conversion is calculated as follows: % conversion=((dried mass/mass withdrawn−initial solids content)×100/(100−initial solids content)). In view of the constant number of active center, the initial solids content for each operation is different (table 3).

TABLE 3

| number of ABu units in the oligomeric alkoxyamine | initial solids content % |
| --- | --- |
| 1 | 3 |
| 3 | 4.5 |
| 8 | 9.9 |
| 10 | 9.7 |
| 15 | 13 |
| 55 | 44 |

TABLE 4

| Number of monomer units incorporated into the alkoxyamine | Dry extract (T° ambient, under vacuum) | % conversion |
| --- | --- | --- |
| 0 | Mass withdrawn: 0.968 g<br>Mass dried: 0.968 g | 100 |
| 1 | Mass withdrawn: 2.110 g<br>Mass dried: 0.411 g | 17 |
| 3 | Mass withdrawn: 0.932 g<br>Mass dried: 0.125 g | 9.3 |
| 8 | Mass withdrawn: 1.762 g<br>Mass dried: 0.477 g | 19.8 |
| 10 | Mass withdrawn: 1.416 g<br>Mass dried: 0.389 g | 19.7 |
| 15 | Mass withdrawn: 4.22 g<br>Mass dried: 1.28 g | 20 |
| 55 | Mass withdrawn: 1.825 g<br>Mass dried: 1.003 g | 20 |

The graph of MMA conversion in 24 h at 47° C. as a function of the number of monomer entities in the alkoxyamine can be seen in FIG. 1. It is observed that, between 1 and 8 monomer units, effective stabilization is obtained. Beyond 8 monomer units, this remains stable.

Example 3

In exactly the same way as in examples 1 and 2, the approach is repeated, replacing the butyl acrylate with styrene.

Styrene was used in place of butyl acrylate to form oligomers of n=3, 8 and 15 monomer units. The oligomers were synthesized in toluene, with a 3.5% by mass percentage of Blocbuilder®. The oligomer is then placed in an MMA solution at a molar concentration of 0.6% of active center at 47° C. (table 4), corresponding to 0.6 mol of alkoxyamine per 100 mol of MMA.

TABLE 4

| | Degree of conversion of MMA (%) after 24 h |
| --- | --- |
| Blocbuilder® | 100% |
| Oligomer n = 3 | <1% |
| Oligomer n = 8 | <1% |
| Oligomer n = 15 | <1% |

After incorporation of the styrene units into the Blocbuilder® alkoxyamine, the oligomeric alkoxyamine remains stable with respect to MMA at 47° C.

This study shows stability of the alkoxyamines containing n units of monomers added, in the presence of reactive monomers at 47° C. The incorporation of the monomer units in the alkoxyamines enables the efficacy of the alkoxyamine to be retained in a reactive monomer environment at 47° C.

Example 4

In this example, the Blocbuilder® was replaced with N-tert-butyl-N-(2-methyl-1-phenylpropyl)-O-(1-phenylethyl)hydroxylamine, which has the following structural formula:

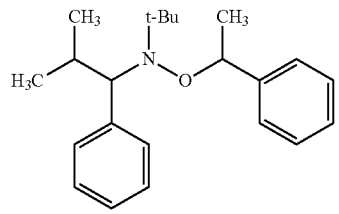 [SMILES: CC(ON(C(c1ccccc1)C(C)C)C(C)(C)C)c1ccccc1]

This alkoxyamine was introduced at 47° C. into a methyl methacrylate solution at 47° C. for 24 h, at a concentration of 0.6%. The same experiment was carried out at 70° C. for 24 h (table 5).

TABLE 5

| | Temperature of the mixture | |
| --- | --- | --- |
| | 47° C. | 70° C. |
| Conversion of methyl methacrylate | 15% | >90% |

At 47° C., the conversion of the MMA is 15% after 24 hours, and more than 90% at 70° C. The alkoxyamine N-tert-butyl-N-(2-methyl-1-phenylpropyl)-O-(1-phenylethyl)hydroxylamine is not stable in an MMA solution at 70° C.

An oligomer based on this alkoxyamine and composed of 12 butyl acrylate units was synthesized at 125° C. in a manner similar to the protocol of example 1. The addition of butyl acrylate units into the alkoxyamine N-tert-butyl-N-(2-methyl-1-phenylpropyl)-O-(1-phenylethyl)hydroxylamine stabilizes the initiating radical in the MMA solution at 70° C. (table 6):

TABLE 6

| | degree of MMA conversion, %, at 24 h |
|---|---|
| N-tert-butyl-N-(2-methyl-1-phenylpropyl)-O-(1-phenylethyl)hydroxylamine | 95 |
| oligomer n = 12 | 5 |

Here again it is found that the alkoxyamine oligomer is much more stable than the nonoligomeric alkoxyamine.

Example 5

In this example, the solvent (toluene) stability of an oligomeric alkoxyamine (Blocbuilder® (ABu$_{15}$)) of example 1 is verified in comparison to its nonoligomeric homolog (Blocbuilder®) from the standpoint of polymerization kinetics.

These two alkoxyamines are left for 4 days in toluene at 20° C. with 0.01 mol % of active center, corresponding to 0.01 mol of alkoxyamine per 100 mol of toluene, typically 305 g of toluene+9.4 g of Blocbuilder® then 600 g of butyl acrylate; 274 g of toluene+56 g of Blocbuilder® (ABu$_{15}$) then 600 g of butyl acrylate.

The solutions are subsequently used for initiating butyl acrylate at 115° C. and the conversions are measured over time, compared with the Blocbuilder® solution used at t=0 for identical initiation of butyl acrylate.

Figure 2:
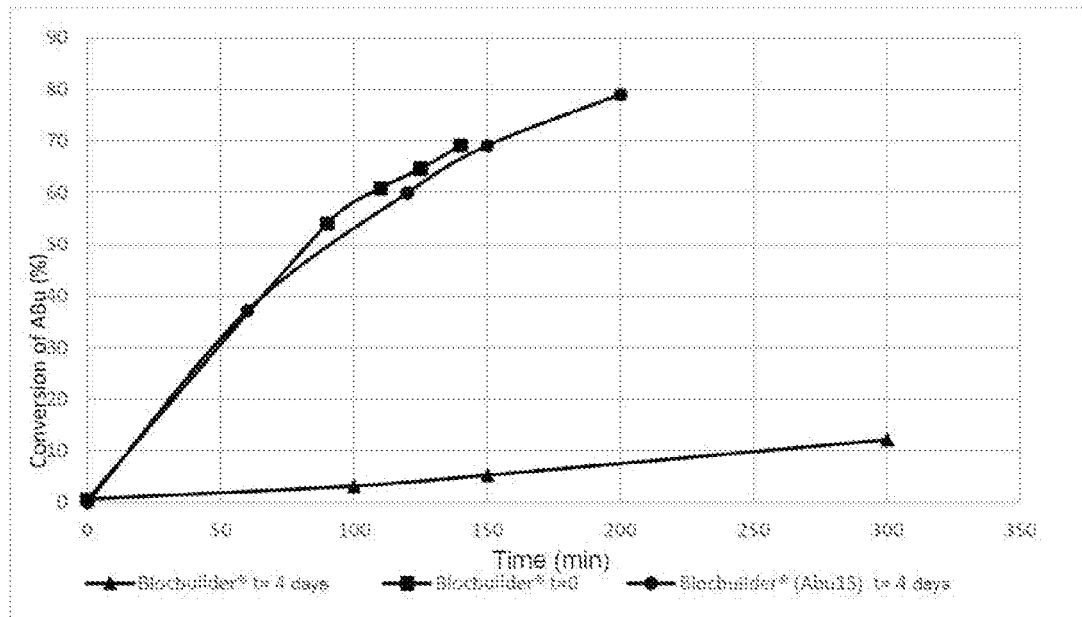
FIG. 2 shows a comparison of the solvent stability of Blocbuilder® and Blocbuilder® ($ABu_{15}$).

It is observed in FIG. 2 that the Blocbuilder® is not stable in a solvent solution at 20° C., in contrast to the Blocbuilder® (ABu$_{15}$)), with the kinetics of polymerization of the butyl acrylate being greatly slowed.

The invention claimed is:

1. An alkoxyamine of formula:

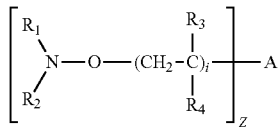

wherein:
i is a value from 1 to 12;
R$_3$ is hydrogen or a hydrocarbon group with or without a heteroatom, and may contain at least one metallic species;
R$_4$ is a cyclic or noncyclic hydrocarbon group with or without a heteroatom, and may contain at least one metallic species;
Z is 1;
fragment

is

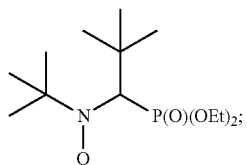

and
fragment A is

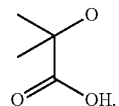

2. A composition comprising the alkoxyamine as claimed in claim 1, a solvent and/or at least one monomer.

* * * * *